United States Patent
Nagasaki et al.

(10) Patent No.: US 7,208,641 B2
(45) Date of Patent: Apr. 24, 2007

(54) METHOD FOR PRODUCING 2,2,2-TRIFLUOROETHANOL

(75) Inventors: Noritaka Nagasaki, Yamaguchi (JP); Tsuyoshi Kawamura, Yamaguchi (JP); Kazunori Nukui, Yamaguchi (JP); Shoji Arai, Yamaguchi (JP)

(73) Assignee: Tosoh F-Tech, Inc., Yamaguchi (JP)

( * ) Notice: Subject to any disclaimer, the term of this patent is extended or adjusted under 35 U.S.C. 154(b) by 509 days.

(21) Appl. No.: 10/489,362

(22) PCT Filed: Sep. 13, 2002

(86) PCT No.: PCT/JP02/09402

§ 371 (c)(1), (2), (4) Date: Mar. 12, 2004

(87) PCT Pub. No.: WO03/024906

PCT Pub. Date: Mar. 27, 2003

(65) Prior Publication Data

US 2004/0254406 A1   Dec. 16, 2004

(30) Foreign Application Priority Data

Sep. 14, 2001 (JP) ............................. 2001-279653
Aug. 22, 2002 (JP) ............................. 2002-241464

(51) Int. Cl.
*C07C 31/24* (2006.01)

(52) U.S. Cl. ........................................ 568/842

(58) Field of Classification Search ............... None
See application file for complete search history.

(56) References Cited

U.S. PATENT DOCUMENTS

| 4,489,211 A | 12/1984 | Ogura et al. ............. 568/842 |
| 4,590,310 A | 5/1986 | Townsend et al. ........ 568/842 |
| 6,894,197 B2 * | 5/2005 | Mimura et al. ........... 568/842 |

FOREIGN PATENT DOCUMENTS

| JP | 58-134043 | 8/1983 |
| JP | 58-140031 | 8/1983 |
| JP | 61-106529 | 5/1986 |

* cited by examiner

*Primary Examiner*—Sikarl A. Witherspoon
(74) *Attorney, Agent, or Firm*—Wenderoth, Lind & Ponack, LLP

(57) ABSTRACT

A method for producing 2,2,2-trifluoroethanol in which a γ-hydroxybutyric acid salt is reacted with 1,1,1-trifluoro-2-chloroethane to generate 2,2,2-trifluoroethanol is provided. This method leads to increased yields of 2,2,2-trifluoroethanol, facilitates the separation of salt byproducts and allows the recycling of an aprotic polar solvent.

The present invention concerns a method for producing 2,2,2-trifluoroethanol in which a γ-hydroxybutyric acid salt is reacted with 1,1,1-trifluoro-2-chloroethane in an aprotic polar solvent to generate 2,2,2-trifluoroethanol. This method is characterized in that the γ-hydroxybutyric acid salt used contains no more than 6 wt % of 4,4'-oxybis(butyric acid).

41 Claims, No Drawings

METHOD FOR PRODUCING 2,2,2-TRIFLUOROETHANOL

This is a 371 of PCT/JP02/09402 filed Sep. 13, 2002, and published as WO03/024906 on Mar. 27, 2003.

TECHNICAL FIELD

The present invention relates to an improved method for producing 2,2,2-trifluoroethanol, in which a salt of γ-hydroxybutyric acid is reacted with 1,1,1-trifluoro-2-chloroethane to produce the desired product. The present invention further relates to a method for producing a salt of γ-hydroxybutyric acid to serve as a material for 2,2,2-trifluoroethanol, as well as to a method for producing 2,2,2-trifluoroethanol by recycling the γ-butyrolactone collected after the reaction.

BACKGROUND ART

Being salts of a hydroxyl-containing organic acid, γ-hydroxybutyric acid salts can partially dissolve in organic solvents. For this reason, γ-hydroxybutyric acid salts are used to hydrolyze organic halides, such as those having alkyl group, alkenyl group, allyl group and other organic functional groups, and serve as a useful reaction reagent to derive corresponding esters and alcohol derivatives.

γ-hydroxybutyric acid salts can be readily obtained by reacting γ-butyrolactone with a hydroxide or a carbonate of an alkali metal or an alkaline earth metal. Since this reaction is generally performed in the presence of water, γ-hydroxybutyric acid salts are obtained as aqueous solutions. To make such solutions usable in reactions such as hydrolysis or esterification, the solutions must be dehydrated to adjust water concentration. This, however, often results in the formation of crystallized γ-hydroxybutyric acid salts. For this reason, a proper aprotic solvent always needs to be selected and used in the reaction.

When an aqueous solution of a γ-hydroxybutyric acid salt is dehydrated, a 4,4'-oxybis(butyric acid) salt, which is an ether dicarboxylic acid formed as a result of the dehydration and subsequent dimerization, is generated as a byproduct (4,4'-oxybis(butyric acid) and its metal salts may be referred to as EDCA and EDCAM, hereinafter). For example, German Patent No. 919167 describes that EDCA is generated at 50 to 55% yields by mixing γ-butyrolactone with a hydroxide of an alkali metal or an alkaline earth metal at 120 to 130° C., then heating the mixture at 180 to 230° C. in the presence of aluminum oxide, and then dehydrating the mixture for 8 to 10 hours. The German patent also describes that EDCA is generated at similar yields even in the absence of aluminum oxide whereas the dehydration takes twice as long. Thus, despite their usefulness as a reagent to promote hydrolysis and other reactions, the preparation of concentrated aqueous solutions of γ-hydroxybutyric acid salts is inevitably accompanied by the generation of EDCAM byproducts.

On the other hand, Japanese Patent Examined Publication Nos. Sho 64-9299 and Sho 64-9300 each disclose a production method for 2,2,2-trifluoromethanol, in which a γ-hydroxybutyric acid salt is reacted with 1,1,1-trifluoro-2-chloroethane in the presence of γ-butyrolactone that serves as an aprotic polar solvent. What is notable about this process is that the γ-butyrolactone, aside from reacting with the alkali metal hydroxide or carbonate to form a γ-hydroxybutyric acid salt as a raw material, serves as a solvent. Not only is the resulting γ-hydroxybutyric acid salt used to directly generate the desired 2,2,2-trifluoroethanol, but it is also converted to γ-butyrolactone after the reaction and can thus be recycled. For these reasons, the process is highly advantageous.

To date, production of 2,2,2-trifluoroethanol has required the γ-hydroxybutyric acid salts produced by the above-described process. The resultant 2,2,2-trifluoroethanol is separated from the reaction mixture by distillation, and the solution remaining in a still after distillation is recycled as an aprotic polar solvent containing γ-butyrolactone. The recycle process involves separating the salt byproduct from the still residue. This separation step has posed many problems. Specifically, the residual solution often becomes excessively viscous and organic materials and solvents may stick to the salt byproduct, making it difficult to separate the salt byproduct by filtration. As a result, a significant solvent loss may occur and the crystallized salt byproduct may form large clumps together with organic materials. In addition, the salt byproducts so produced are often unsuitable for use as fertilizers and may result in increased amounts of waste material. Each of these problems is critical to an industrial process and must be eliminated.

DISCLOSURE OF THE INVENTION

In an effort to eliminate the above-described problems of the current production process of 2,2,2-trifluoroethanol, the present inventors first sought the causes of these problems and concluded that EDCA and EDCAM were the major factors. Specifically, the present inventors found that these byproducts are mostly generated during the production of γ-hydroxybutyric acid salt and gradually accumulate as the γ-butyrolactone solvent is repeatedly recycled as an aprotic polar solvent, thereby causing the aforementioned problems.

Thus, the present inventors devoted much effort to finding a way to minimize the generation of EDCA and EDCAM and found that this can be achieved by carrying out the production process of γ-hydroxybutyric acid salt under particular conditions. The present inventors also conducted studies to develop a technique for effectively removing/separating the EDCA and EDCAM byproducts from the collected γ-butyrolactone and found that this can be done by subjecting the γ-butyrolactone to two-layer separation under particular conditions. Once depleted of the EDCA and EDCAM byproducts, the γ-butyrolactone can be reused in subsequent processes.

Accordingly, a first objective of the present invention concerns a method for producing 2,2,2-trifluoroethanol in which a γ-hydroxybutyric acid salt is reacted with 1,1,1-trifluoro-2-chloroethane in an aprotic polar solvent to generate 2,2,2-trifluoroethanol. Such an objective is achieved by providing a production method that leads to increased yields of 2,2,2-trifluoroethanol, facilitates the separation of salt byproducts and allows the recycling of an aprotic polar solvent.

A second objective of the present invention is to provide a method for producing a γ-hydroxybutyric acid salt containing a reduced amount of EDCA. Such a γ-hydroxybutyric acid salt is suitable for use as a material for the production of 2,2,2-trifluoroethanol.

A third objective of the present invention is to provide a method for producing 2,2,2-trifluoroethanol that allows γ-butyrolactone to be recycled for industrial use. Specifically, γ-butyrolactone to serve both as a reactant and a solvent in the production of 2,2,2-trifluoroethanol is collected and is depleted of EDCA by allowing it to separate into two layers.

The present inventors have found that the flaws of conventional production processes of 2,2,2-trifluoroethanol are caused by the presence of EDCA and EDCAM, which are mostly generated during the production of γ-hydroxybutyric acid salt. The inventors have also found that these byproducts accumulate through repeated use of the γ-butyrolactone solvent to bring about the aforementioned problems. The present inventors have further found that the generation of EDCA and EDCAM can be minimized by carrying out the production process of γ-hydroxybutyric acid salt under particular conditions and that the EDCA and EDCAM byproducts can be removed from the collected γ-butyrolactone by subjecting the γ-butyrolactone to a two-layer separation process under particular conditions. Once depleted of the EDCA and EDCAM byproducts, the γ-butyrolactone can be reused in subsequent processes. These findings ultimately led the present inventors to devise the invention.

Accordingly, a first invention concerns a method for producing 2,2,2-trifluoroethanol in which 1,1,1-trifluoro-1-chloroethane is reacted with a γ-hydroxybutyric acid salt-material system containing an aprotic polar solvent and a γ-hydroxybutyric acid salt to generate 2,2,2-trifluoroethanol. This method is characterized in that the γ-hydroxybutyric acid salt-material system contains no more than 6 wt % of 4,4'-oxybis(butyric acid).

A second invention concerns the first invention and is characterized in that a solution remaining in a still after 2,2,2-trifluoroethanol has been removed by distillation from a reaction mixture is reused as the aprotic polar solvent. The reaction mixture is one that results after γ-hydroxybutyric acid salt has been reacted with 1,1,1-trifluoro-2-chloroethane in the aprotic polar solvent.

A third invention concerns the first or the second invention and is characterized in that the γ-hydroxybutyric acid salt-material system comprises a γ-hydroxybutyric acid salt prepared by reacting, in the aprotic polar solvent, γ-butyrolactone with one or two or more selected from the group consisting of an alkali metal hydroxide, an alkali metal carbonate, an alkaline earth metal hydroxide and an alkaline earth metal carbonate. The γ-hydroxybutyric acid salt is obtained by dehydrating, during or after the reaction, the reaction mixture to a water concentration of 0.2 to 8 wt % at a temperature of 170° C. or below.

A fourth invention concerns the first, the second or the third invention and is characterized in that the aprotic polar solvent is γ-butyrolactone.

A fifth invention concerns the third invention and is characterized in that the alkali metal is potassium.

A sixth invention concerns the third, the fourth or the fifth invention and is characterized in that the dehydration is achieved by reduced-pressure distillation carried out at 150° C. or below.

A seventh invention concerns the third, the fourth, the fifth or the sixth invention and is characterized in that the dehydration is completed within a time period of 15 hours or less.

An eighth invention concerns a method for producing a γ-hydroxybutyric acid salt-material system, in which γ-butyrolactone is reacted in an aprotic polar solvent with one or two or more selected from the group consisting of an alkali metal hydroxide, an alkali metal carbonate, an alkaline earth metal hydroxide and an alkaline earth metal carbonate. This method is characterized in that the reaction mixture is dehydrated, during or after the reaction, to a water concentration of 0.2 to 8 wt % at a temperature of 170° C. or below.

A ninth invention concerns the eighth invention and is characterized in that the aprotic polar solvent is γ-butyrolactone.

A tenth invention concerns the eighth invention and is characterized in that the alkali metal is potassium.

An eleventh invention concerns the eighth, the ninth or the tenth invention and is characterized in that the dehydration is achieved by reduced-pressure distillation carried out at 150° C. or below.

A twelfth invention concerns the eighth, the ninth, the tenth, or the eleventh invention and is characterized in that the dehydration is completed within a time period of 15 hours or less.

A thirteenth invention concerns a method for producing 2,2,2-trifluoroethanol characterized in that the γ-hydroxybutyric acid salt-material system produced by the method according to the eighth, the ninth, the tenth, the eleventh, or the twelfth invention is reacted with 1,1,1-trifluoro-2-chloroethane.

A fourteenth invention concerns a method for producing 2,2,2-trifluoroethanol in which 1,1,1-trifluoro-2-chloroethane is reacted with a γ-hydroxybutyric acid salt-material system comprising γ-butyrolactone and potassium γ-hydroxybutyrate to generate 2,2,2-trifluoroethanol. The method comprises the steps of:

reacting the γ-hydroxybutyric acid salt-material system with 1,1,1-trifluoro-2-chloroethane to obtain a reaction mixture;

separating 2,2,2-trifluoroethanol by distillation from the reaction mixture to obtain a solution in a still, removing potassium chloride byproducts from the still solution to obtain a solvent;

removing 4,4'-oxybis(butyric acid) by allowing the solution to stand to separate it into two layers; and recycling the collected solution as a material for potassium γ-hydroxybutyrate and/or the γ-butyrolactone of the γ-hydroxybutyric acid salt-material system.

A fifteenth invention concerns the fourteenth invention and is characterized in that the collected solution contains no more than 6 wt % of 4,4'-oxybis(butyric acid).

A sixteenth invention concerns the fourteenth or the fifteenth invention and is characterized in that the removal of 4,4'-oxybis(butyric acid) by the two-layer separation is carried out at a temperature of 0° C. to 50° C.

A seventeenth invention concerns the fourteenth, the fifteenth or the sixteenth invention and is characterized in that the solvent is allowed to stand for at least one hour.

An eighteenth invention concerns the fourteenth, the fifteenth, the sixteenth or the seventeenth invention and is characterized in that the γ-hydroxybutyric acid salt-material system comprises a reaction mixture obtained by mixing the purified collected γ-butyrolactone with an aqueous solution of potassium hydroxide and subsequently dehydrating the mixture.

BEST MODE FOR CARRYING OUT THE INVENTION

The present invention concerns a method for producing 2,2,2-trifluoroethanol in which 2,2,2-trifluoroethanol is produced by reacting 1,1,1-trifluoro-2-chloroethane with a γ-hydroxybutyric acid salt-material system containing an aprotic polar solvent and a γ-hydroxybutyric acid salt. The method is characterized in that the γ-hydroxybutyric acid salt-material system used contains no more than 6 wt % of EDCA. The use of such material system eliminates the above-described problems, namely, the organic materials and solvents sticking to the salt byproducts, which makes it difficult to separate the salt byproducts by filtration and results in a significant solvent loss; the salt byproduct crystals forming large clumps together with organic materials; the salt byproducts becoming unsuitable for use as fertilizers; or the amount of waste material being increased.

To prepare the γ-hydroxybutyric acid salt-material system of the present invention, which advantageously contains no more than 6 wt % of EDCA, one, two, or more selected from alkali metal hydroxides, alkali metal carbonates, alkaline earth metal hydroxides, and alkaline earth metal carbonates are reacted with γ-butyrolactone in an aprotic polar solvent and, during or after the reaction, water is removed from the reaction mixture at a temperature of 170° C. or below to a water concentration of 0.2 to 8 wt %.

As used herein, the term "EDCA content" is the amount defined by the following equation:

EDCA content (%)=EDCA(g)×100/(aprotic polar solvent(g)+γ-hydroxybutyric acid salt(g)+EDCA (g)+water(g))     (1)*

* When EDCAM is contained in the γ-hydroxybutyric acid salt-material system, the amount of EDCAM is converted to the amount of EDCA.

The term "γ-hydroxybutyric acid salt" as used herein refers to an alkali metal salt or an alkaline earth metal salt of γ-hydroxybutyric acid.

2,2,2-trifluoroethanol can be readily prepared in high yield by reacting the γ-hydroxybutyric acid salt-material system prepared in the above-described manner with 1,1,1-trifluoro-2-chloroethane in the presence of an aprotic polar solvent. The desired 2,2,2-trifluoroethanol is then removed from the resulting reaction mixture by distillation or other proper separation techniques. By simply removing the salt byproducts from the aprotic solution remaining in a still, the residual solution can be reused as the aprotic polar solvent without further purification. In this manner, 2,2,2-trifluoroethanol can be obtained in high yield while the EDCA concentration in the aprotic polar solvent can be maintained at 6 wt % or lower for a prolonged time through repeated use of the solvent under the above-described condition.

When γ-butyrolactone is used as the aprotic polar solvent in the present invention and it is desired to maintain the EDCA concentration at 6 wt % or lower for an extended period of time through repeated use of the solvent, 1,1,1-trifluoro-2-chloroethane is reacted with the γ-hydroxybutyric acid salt material-system, which contains γ-butyrolactone along with potassium γ-hydroxybutyrate, and 2,2,2-trifluoroethanol is separated from the reaction mixture by distillation. The potassium chloride byproduct is then removed from the solution remaining in the still and the residual solvent is allowed to stand to separate and remove the EDCA and/or EDCAM by two-layer separation. The remaining γ-butyrolactone solution can then be recycled as a material for the potassium γ-hydroxybutyrate and/or in the γ-hydroxybutyric acid salt-material system.

In this manner, increases in the viscosity of the solvent can be avoided, as can the sticking of substantial amounts of organic materials to the salt byproduct and the significant loss of the solvent. In addition, this method does not result in significant amounts of waste material produced or the salt byproduct crystals forming large clumps, thus facilitating the filtration process. Furthermore, the salt byproducts formed by this method are suitable for use as fertilizers.

The present invention will now be described in further detail.

The aprotic polar solvents for use in the present invention include γ-butyrolactone, N-methyl-2-pyrrolidone, 1,3-dimethyl-2-imidazolidinone, sulfolane, dimethylsulfoxide, dimethylformamide, and dimethylacetamide. Of these, particularly preferred are γ-butyrolactone, N-methyl-2-pyrrolidone, 1,3-dimethyl-2-imidazolidinone, and sulfolane, with γ-butyrolactone being most preferred. γ-butyrolactone serves as an aprotic polar solvent and as a reaction reagent, acting as so-called a reaction solvent. When necessary, these solvents may be used individually or as a mixed solvent consisting of one or more solvents. The aprotic polar solvent may be a commercially available product, or it may be a solvent recycled after used in the production of 2,2,2-trifluoroethanol and depleted of the salt byproducts. The recycled solvent may be used unpurified.

If γ-butyrolactone is used as the aprotic polar solvent, the solvent can be recycled for an even longer period. In this respect, γ-butyrolactone includes what is obtained after the solvent has been used in the production of 2,2,2-trifluoroethanol and has then been depleted of the salt byproducts. The γ-butyrolactone may be used without further processing or it may be a solution collected after purified in a purification process, which will be described later. When necessary, a commercially available product may be added as desired. The γ-butyrolactone serves not only as a solvent during the reaction of γ-hydroxybutyric acid salt-material system with 1,1,1-trifluoro-2-chloroethane to generate 2,2,2-trifluoroethanol but also as a starting material and/or a solvent for the production of potassium γ-hydroxybutyrate. For this reason, it is preferred that the γ-butyrolactone contains no more than 6 wt % of EDCA. If the amount of EDCA in the γ-butyrolactone exceeds 6 wt % when γ-butyrolactone is to serve as the starting material for the production of γ-hydroxybutyric acid salt, then some of the alkali added is consumed by EDCA, thus making it difficult to obtain a desired amount of the γ-hydroxybutyric acid salt. On the other hand, if the amount of EDCA exceeds 6 wt % when γ-butyrolactone is to serve as the solvent, then the aforementioned problems of the process will result. In this case, a commercially available product is used as the γ-butyrolactone in the first round of the reaction. The γ-butyrolactone is recycled in the second and succeeding rounds and used without further processing or after purified in a purification process, which will be described later.

In the present invention, the starting materials for the production of γ-hydroxybutyric acid salt may include one or two or more inorganic compounds selected from alkali metal hydroxides, alkali metal carbonates, alkaline earth metal hydroxides, and alkaline earth metal carbonates. Examples of such compounds include hydroxides and carbonates of lithium, sodium, potassium, and calcium. Hydroxides and carbonates of potassium are particularly preferred. The potassium hydroxides may be provided in the form of an aqueous solution of a commercially available potassium hydroxide or a commercially available aqueous solution of potassium hydroxide. The concentration of the aqueous solution of potassium hydroxide is preferably in the range of 10 to 48 wt % although such a solution may have any concentration. The potassium carbonate may be provided in the form of potassium carbonate and/or potassium bicarbonate. Commercially available potassium carbonate products may be used without any processing. The potassium carbonate provided in the form of powder may also be used by dissolving it in water, if necessary.

According to the present invention, the above-described materials are used to prepare the γ-hydroxybutyric acid salt-material system. How this can be done will now be explained by taking an example in which γ-butyrolactone is used along with a 48% aqueous solution of potassium hydroxide. Predetermined amounts of an aprotic polar solvent and γ-butyrolactone to serve as a starting material are placed in a reactor equipped with a thermometer, a stirrer, dropping equipment, and a pressure reducing device. While the mixture is constantly stirred, a predetermined amount of the aqueous solution of potassium hydroxide is delivered dropwise from the dropping equipment to produce potassium γ-hydroxybutyrate. Since the reaction is an exothermic reaction that proceeds quantitatively, water is added as desired for cooling. The amount of the potassium hydroxide added is adjusted so that the amount of the resulting potassium γ-hydroxybutyrate is preferably no more than 30 wt % with respect to the aprotic polar solvent. The potassium γ-hydroxybutyrate, when generated in an amount greater than 30 wt %, can make the reaction mixture excessively viscous and can thereby make the stirring of the mixture and, thus, the dehydration process difficult.

The reaction of γ-butyrolactone with potassium hydroxide is shown by the following chemical equation:

[Chemical Equation]

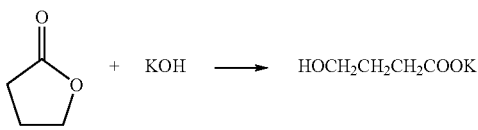

According to the present invention, the aprotic polar solvent containing potassium γ-hydroxybutyrate is then dehydrated by heating. The dehydration is done by atmospheric distillation or reduced-pressure distillation at a temperature of 170° C. or below, preferably 150° C. or below. In the case of reduced-pressure distillation, pressure is reduced to for example about 0.07 to 0.67 MPa. Preferably, the dehydration process is carried out within a time period not exceeding 15 hours and is continued until the water content in the aprotic polar solvent is from 0.2 to 8 wt %. The process exceeding 15 hours tends to result in a substantial amount of EDCAM generated. Also, the water content of the aprotic polar solvent that exceeds 8 wt % may lead to a significant decrease in the rate of the subsequent hydrolysis of 1,1,1-trifluoro-2-chloroethane and is thus unfavorable.

According to the present invention, once dehydrated, the potassium γ-hydroxybutyrate-containing aprotic polar solvent is transferred to a pressurized container, in which it is reacted with 1,1,1-trifluoro-2-chloroethane to produce 2,2,2-trifluoroethanol. 1,1,1-trifluoro-2-chloroethane used in this process may be obtained by a known method, for example, by using trichloroethylene with hydrofluoric acid in the presence of a catalyst. Preferably, 1,1,1-trifluoro-2-chloroethane has a 98% or higher purity although it may have any suitable purity. The 1,1,1-trifluoro-2-chloroethane may contain 1,1,2-tetrafluoroethane (134a) or any other impurity that is not involved in the present reaction.

According to present invention, the procedures and conditions for the reaction can be properly selected as described in examples in this description. For example, the above-described potassium γ-hydroxybutyrate-containing aprotic polar solvent is placed in a pressurized container along with 1,1,1-trifluoro-2-chloroethane and the reaction is allowed to proceed at 180 to 220° C. for 3 to 8 hours until completion while the reaction mixture is constantly stirred. After the unreacted 1,1,1-trifluoro-2-chloroethane has been purged, the reaction mixture is collected and is then distilled. As a result, the desired 2,2,2-trifluoroethanol product is separated. Meanwhile, the residue remaining in the still after distillation takes the form of a slurry and comprises a γ-butyrolactone-containing aprotic polar solution and a potassium chloride byproduct. The potassium chloride is separated as a solid by filtration, centrifugation or other solid-liquid separation techniques. The γ-butyrolactone-containing aprotic polar solution collected in the solid-liquid separation process is then recycled, without further processing, to serve as the solvent or the material of potassium γ-hydroxybutyrate in the next round of the reaction. After separation, the aprotic polar solution contains no more than 6 wt % of EDCA. Should the amount of EDCA exceed 6 wt %, significant problems may arise, such as a decrease in the yield of 2,2,2-trifluoroethanol; an increased viscosity, which makes the filtration process difficult; a significant amount of organic materials sticking to the salt byproducts; a substantial solvent loss; an increased amount of waste material; or the salt byproduct crystals forming clumps.

According to the present invention, when the aprotic nonpolar solvent is γ-butyrolactone and it is desired to recycle the solvent for an extended period of time, the γ-butyrolactone solvent, collected in the solid-liquid separation step as described above, is left to stand to allow it to separate into two layers for purification. This process does not require special techniques or apparatuses and can be done by simply allowing the solvent to stand undisturbed. This allows the solvent to separate into two layers with the top γ-butyrolactone layer containing 6 wt % or less EDCA. This top layer can be collected and recycled.

According to the present invention, the process of leaving the solvent for separating it into two layers is preferably carried out at a temperature of 0° C. to 50° C., and more preferably at a temperature of 0° C. to 40° C. If the process is carried out at a temperature of above 50° C., not only does it take a substantial amount of time for the solvent to separate into two layers, but the EDCA content in the top γ-butyrolactone layer or the collected solution is also somewhat increased. In comparison, if the solvent is to be cooled to below 0° C., a large facility is required.

According to the present invention, while the solvent may be left to stand for any time length to allow it to separate into two layers, it needs to be left for at least 1 hour. When left for too short a time period, the solvent does not completely separate into two layers and the EDCA content in the top γ-butyrolactone layer or the collected solution is somewhat increased. According to the present invention, the above-described purification process may be carried out as frequently as desired: the solvent may be left to stand for removing EDCA each time the solvent is collected or after repeatedly used in the reaction.

According to the present invention, the collected solvent, which has been purified by removing EDCA and/or EDCAM in the two-layer separation process as described above, is recycled as a solvent for use in the production of 2,2,2-trifluoroethanol and/or as a material for 2,2,2-trifluoroethanol. As a result, no significant problems regarding the process arise as a result of the repetitive use of the γ-butyrolactone solvent to serve as a solvent and/or a material in the industrial production of 2,2,2-trifluoroethanol. In this regard, the γ-butyrolactone solvent can be recycled without any special processing. Specifically, many of the problems associated with the conventional process have been eliminated, such as the solution becoming excessively viscous; significant amounts of organic materials adhering to the salt byproducts; significant amounts of solvent being lost; waste materials produced in large quantity; the salt byproduct crystals forming clumps, making filtration difficult. The problem of the salt byproducts becoming unsuitable for use as fertilizers is also avoided. According to the present invention, the collected solvent can be purified and recycled as many times as desired.

The reaction of potassium γ-hydroxybutyrate with 1,1,1-trifluoro-2-chloroethane is shown by the following chemical equations:

[Chemical Equation]

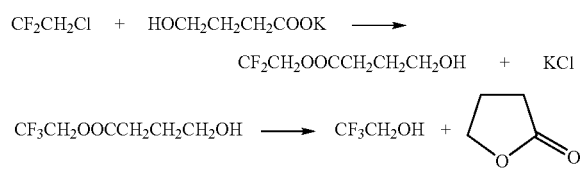

EXAMPLES

The present invention will now be described with reference to Examples, which are provided by way of example only and are not intended to limit the scope of the invention in any way.

Example 1

650 g (7.55 mol) γ-butyrolactone was placed in a 1000 ml flask equipped with a reduced pressure distillation apparatus, a thermometer, a stirrer, and a dropping funnel. 102 g of a 48% aqueous solution of potassium hydroxide (0.873 mol potassium hydroxide) was poured in the dropping funnel and was added dropwise approximately over 40 minutes while being stirred. The addition of the solution caused the reaction mixture to gradually generate heat and the internal temperature rose to approximately 50° C. The pressure of the system was reduced to 0.4 MPa and the reaction mixture was distilled for 12 hours to remove water while it was gradually heated to 145° C.

The resulting γ-butyrolactone solution contained 17.2 wt % potassium γ-hydroxybutyrate. A portion of this solution was neutralized with hydrochloric acid and was subjected to HPLC analysis. The results of the analysis indicated that no EDCA (4,4'-oxybis(butyric acid)) was generated. The water content of the γ-butyrolactone solution was analyzed by Karl Fischer technique and was determined to be 3.4 wt %.

Example 2

Potassium γ-hydroxybutyrate was synthesized in the same manner as in Example 1, except that water was distilled out at 165° C. and the pressure of the system was reduced to 0.8 MPa.

The resulting γ-butyrolactone solution contained 17.0 wt % potassium γ-hydroxybutyrate. A portion of this solution was neutralized with hydrochloric acid and was subjected to HPLC analysis. The results of the analysis indicated that 0.2 wt % EDCA (4,4'-oxybis(butyric acid)) was generated. The water content of the γ-butyrolactone solution was analyzed by Karl Fischer technique and was determined to be 3.3 wt %.

Example 3

Potassium γ-hydroxybutyrate was synthesized in the same manner as in Example 1, except that the distillation was continued for 18 hours.

The resulting γ-butyrolactone solution contained 16.6 wt % potassium γ-hydroxybutyrate. A portion of this solution was neutralized with hydrochloric acid and was subjected to HPLC analysis. The results of the analysis indicated that 0.8 wt % EDCA (4,4'-oxybis(butyric acid)) was generated. The water content of the γ-butyrolactone solution was analyzed by Karl Fischer technique and was determined to be 3.5 wt %.

Example 4

Potassium γ-hydroxybutyrate was synthesized in the same manner as in Example 1, except that the amount of the 48% aqueous solution of potassium hydroxide used was 158 g (1.35 mol potassium hydroxide).

The addition of potassium hydroxide caused the internal temperature to rise to approximately 70° C. The resulting γ-butyrolactone solution contained 25.2 wt % potassium γ-hydroxybutyrate. A portion of this solution was neutralized with hydrochloric acid and was subjected to HPLC analysis. The results of the analysis indicated that 0.3 wt % EDCA (4,4'-oxybis(butyric acid)) was generated. The water content of the γ-butyrolactone solution was analyzed by Karl Fischer technique and was determined to be 3.7 wt %.

Example 5

Potassium γ-hydroxybutyrate was synthesized in the same manner as in Example 1, except that 521 g N-methylpyrrolidone and 129 g γ-butyrolactone (1.80 mol) were used in place of γ-butyrolactone.

The resulting γ-butyrolactone solution contained 17.0 wt % potassium γ-hydroxybutyrate. A portion of this solution was neutralized with hydrochloric acid and was subjected to HPLC analysis. The results of the analysis indicated that no EDCA (4,4'-oxybis(butyric acid)) was generated. The water content of the γ-butyrolactone solution was analyzed by Karl Fischer technique and was determined to be 4.2 wt %.

Example 6

700 g of the potassium γ-hydroxybutyrate solution obtained in Example 1 were transferred to a 1000 mL SUS316 autoclave equipped with a magnetic stirrer. The autoclave was sealed and the atmosphere inside was replaced with nitrogen three times. 150 g (1.27 mol) of 1,1,1-trifluoro-2-chloroethane were added from a pressurized container. The mixture was heated to 200° C. while being stirred and the reaction was allowed to proceed for 6 hours under a pressure of 1.5 MPa. Subsequently, the autoclave was cooled to 150° C. and a trap cooled to approximately 0° C. was attached to the opening of the autoclave. The pressure inside was then slowly reduced to purge the unreacted 1,1,1-trifluoro-2-chloroethane. The resulting 2,2,2-trifluoroethanol product was completely removed by distillation while the reaction mixture was stirred by the magnetic stirrer. The yield of the product was 96% with respect to potassium γ-hydroxybutyrate. The autoclave was then allowed to cool to room temperature to collect in a still a solution containing γ-butyrolactone and potassium chloride byproduct. The still solution was then filtered through a G3 glass filter to separate the potassium chloride byproduct. As a result, a light brown γ-butyrolactone solvent having a normal viscosity was obtained. The salt byproduct was readily separated by filtration and was obtained as a white powder.

Example 7

Using the γ-butyrolactone-containing still solution obtained in Example 6, the procedures of Example 1 and Example 6 were repeated 6 times. After each batch process, 2,2,2-trifluoroethanol was obtained at 94 to 98% yield (with respect to potassium hydroxide). After each round of the repeating process, a few grams of γ-butyrolactone were supplied to compensate for the material lost by the sampling and each procedure. After 6 rounds, the still solution turned dark brown but still maintained normal viscosity. The salt byproduct was obtained as a slightly yellow brownish powder and was readily separated by filtration through G3 glass filter. A portion of this solution was neutralized with hydrochloric acid and was subjected to HPLC analysis. The results of the analysis indicated that the solution contained 1.5% EDCA (4,4'-oxybis(butyric acid)).

Example 8

A γ-butyrolactone solvent containing a significant amount of EDCA (EDCA content=8.0 wt %) was obtained in the manner described in Comparative Example 2, which will be described later. A portion of the solvent was allowed to stand at 50° C. for 30 hours to separate it into two layers. The top layer, the γ-butyrolactone solution layer to be collected, contained 3.9 wt % of EDCA.

The top layer was collected and was used to produce 2,2,2-trifluoroethanol. Specifically, 150 g γ-butyrolactone (1.74 mol assuming it consists sorely of γ-butyrolactone) was placed in a 300 ml flask equipped with a reduced pressure distillation apparatus, a thermometer, a stirrer, and a dropping funnel. 23.5 g of a 48% aqueous solution of potassium hydroxide (0.20 mol potassium hydroxide) were poured into the dropping funnel and were added dropwise over approximately 40 minutes while being stirred. The addition of the solution caused the reaction mixture to gradually generate heat and the internal temperature rose to approximately 50° C. The pressure of the system was reduced to 0.4 MPa and the reaction mixture was distilled for 12 hours to remove water while it was gradually heated to 145° C. The resulting solution of potassium γ-hydroxybutyrate contained 4.4 wt % EDCA and 3.6 wt % water. 165 g of the potassium γ-hydroxybutyrate solution were transferred to a 300 ml SUS316 autoclave equipped with a magnetic stirrer. The autoclave was sealed and the atmosphere inside was replaced with nitrogen three times. 35.3 g (0.30 mol) of 1,1,1-trifluoro-2-chloroethane were added from a pressurized container. The mixture was heated to 200° C. while being stirred and the reaction was allowed to proceed for 6 hours under a pressure of 1.5 MPa. Subsequently, the autoclave was cooled to 150° C. and a trap cooled to approximately 0° C. was attached to the opening of the autoclave. The pressure inside was then slowly reduced to purge the unreacted 1,1,1-trifluoro-2-chloroethane. The resulting 2,2,2-trifluoroethanol product was completely removed by distillation while the reaction mixture was stirred by the magnetic stirrer. The yield of the product was 95% with respect to potassium γ-hydroxybutyrate. The autoclave was then allowed to cool to room temperature to collect in a still a solution containing γ-butyrolactone and potassium chloride byproduct. The still solution was then filtered through a G3 glass filter to separate the potassium chloride byproduct. As a result, a dark brown γ-butyrolactone solvent was collected. Containing 4.8 wt % EDCA, the solvent had a normal viscosity and was of the nature that did not cause any process-related problem, such as filtration taking too long.

Example 9

Purification was carried out in the same manner as in Example 8, except that the γ-butyrolactone solvent was allowed to stand at 25° C. for 15 hours to separate it in two layers. The top layer, the γ-butyrolactone solution layer to be collected, contained 3.3 wt % of EDCA.

Example 10

Purification was carried out in the same manner as in Example 8, except that the γ-butyrolactone solvent was allowed to stand at 0° C. for 1 hour to separate it in two layers. The top layer, the γ-butyrolactone solution layer to be collected, contained 3.1 wt % of EDCA.

Example 11

To purify the collected γ-butyrolactone, 2,2,2-trifluoroethanol was produced in a 5 $m^3$ γ-butyrolactone-purification tank with a top outlet. After the reaction had been completed, the potassium chloride byproduct was separated by filtration and the collected γ-butyrolactone solvent was reused to serve both as material and solvent for the reaction without further processing. A commercially available γ-butyrolactone product was supplied in an amount required to compensate for the γ-butyrolactone lost along with the potassium chloride byproduct. After 3 months of repeating this cycle, the EDCA content in the collected γ-butyrolactone solvent reached 5.9%. At this stage, the collected γ-butyrolactone solvent was placed in the purification tank and was allowed to stand at 25° C. for 10 hours for purification. As a result, the solvent separated into two layers and the EDCA content in the top layer, the γ-butyrolactone solvent layer to be collected, was decreased to 2.7%. In contrast, the bottom layer of the γ-butyrolactone solution contained significant amounts of water, KCl, and EDCA.

Comparative Example 1

A potassium γ-hydroxybutyrate solution was prepared in the same manner as in Example 1, except that the distillation to remove water was carried out at 190 to 200° C. for 20 hours under atmospheric pressure. The resulting γ-butyrolactone solution contained 11.2 wt % potassium γ-hydroxybutyrate.

A portion of this solution was neutralized with hydrochloric acid and was subjected to HPLC analysis. The results of the analysis indicated that 7 wt % EDCA (4,4'-oxybis (butyric acid)) was generated. The water content of the γ-butyrolactone solution was analyzed by Karl Fischer technique and was determined to be 4.5%.

Comparative Example 2

Using the potassium γ-hydroxybutyrate solution obtained in Comparative Example 1, 2,2,2-trifluoroethanol was produced in the same manner as in Example 6. Subsequently, the same procedures as in Example 6 were followed to obtain a solution in a still. The yield of 2,2,2-trifluoroethanol was 91%. The still solution was then filtered through a G3 glass filter to separate the potassium chloride byproduct. As a result, a light brown γ-butyrolactone solvent having a relatively high viscosity was obtained. The salt byproduct was obtained as a white powder with some organic material adhering to it. The filtration of the salt product took considerable time and was extremely difficult. The collected γ-butyrolactone solution contained 8.0 wt % EDCA.

Comparative Example 3

A potassium γ-hydroxybutyrate solution was synthesized in the same manner as in Example 1, except that 242 g of a 48% aqueous solution of potassium hydroxide (2.00 mol potassium hydroxide) were used, that the internal temperature was raised to 120° C., and that the distillation to remove water was carried out at 200° C. for 24 hours under atmospheric pressure. The resulting γ-butyrolactone solution contained 13.1 wt % potassium γ-hydroxybutyrate. The solution was extremely viscous and was difficult to stir.

A portion of this solution was neutralized with hydrochloric acid and was subjected to HPLC analysis. The results of the analysis indicated that 35.8 wt % EDCA (4,4'-oxybis (butyric acid)) was generated. The water content of the γ-butyrolactone solution was analyzed by Karl Fischer technique and was determined to be 6.4%.

When the γ-butyrolactone solution was used in hydrolysis, the reaction rate was low. Subsequently, the same procedures as in Example 6 were followed to separate 2,2,2-trifluoroethanol and obtain a still solution. The yield of 2,2,2-trifluoroethanol was 86%. No potassium salt was separated after one-hour filtration of the solution.

Comparative Example 4

A potassium γ-hydroxybutyrate solution was prepared in exactly the same manner as in Example 1. The pressure of the system was reduced to 0.4 MPa and the reaction mixture was distilled for 15 hours to thoroughly remove water while it was gradually heated to 145° C. The water content of the γ-butyrolactone solution was analyzed by Karl Fischer technique and was determined to be 0.1 wt %.

700 g of the potassium γ-hydroxybutyrate solution were transferred to a 1000 ml SUS316 autoclave equipped with a magnetic stirrer. The autoclave was sealed and the atmosphere inside was replaced with nitrogen three times. 150 g (1.27 mol) of 1,1,1-trifluoro-2-chloroethane were added from a pressurized container. The mixture was heated to 200° C. while being stirred and the reaction was allowed to proceed for 6 hours. Subsequently, the same procedures as in Example 6 were followed to separate 2,2,2-trifluoroethanol and obtain a still solution. The yield of 2,2,2-trifluoroethanol was 73%. No potassium salt was separated after one-hour filtration of the solution.

Comparative Example 5

650 g (7.55 mol) of γ-butyrolactone and 49 g of pellets of solid potassium hydroxide were placed in a 1000 ml SUS316 autoclave equipped with a magnetic stirrer. The autoclave was sealed and the atmosphere inside was replaced with nitrogen three times. 150 g (1.27 mol) of 1,1,1-trifluoro-2-chloroethane were added from a pressurized container. The mixture was heated to 200° C. while being stirred and the reaction was allowed to proceed for 6 hours under a pressure of 1.5 MPa. Subsequently, the autoclave was cooled to room temperature. The pressure inside was then slowly reduced to purge the unreacted 1,1,1-trifluoro-2-chloroethane. Subsequently, the same procedures as in Example 6 were followed to separate 2,2,2-trifluoroethanol and obtain a still solution. The yield of 2,2,2-trifluoroethanol was 68%. No potassium salt was separated after one-hour filtration of the solution.

Comparative Example 6

Potassium γ-hydroxybutyrate was synthesized in the same manner as in Example 1, except that the reaction mixture was distilled for 8 hours to remove water. A portion of the potassium γ-hydroxybutyrate was taken and was analyzed for the water content by Karl Fischer technique. The results of the analysis indicated that the reaction mixture contained 10.1 wt % water.

Using 700 g of the potassium γ-hydroxybutyrate solution, the reaction was carried out in the same manner as in Example 6. After the reaction, 114 g of unreacted 1,1,1-trifluoro-2-chloroethane were collected, indicating that only 27% of the reactant (as determined by the amount of potassium hydroxide) had reacted.

Comparative Example 7

Purification was carried out in exactly the same manner as in Example 10, except that the γ-butyrolactone solvent was allowed to stand for 30 minutes. The solvent did not separate into two layers and thus could not be purified. Using the resulting solvent without further processing, 2,2,2-trifluoroethanol was produced in exactly the same manner as in Example 8. As a result, the yield of 2,2,2-trifluoroethanol was 78%. The potassium chloride byproduct was separated by filtration through a G3 glass filter. As a result, a dark brown γ-butyrolactone having a relatively high viscosity was obtained. The salt byproduct was obtained as a light yellow powder with some organic material adhering to it. The filtration of the salt product took considerable time and was difficult. According to analytical result, the separated γ-butyrolactone solution contained 8.7 wt % EDCA.

Comparative Example 8

Purification was carried out in exactly the same manner as in Example 9, except that the γ-butyrolactone solvent was allowed to stand at 60° C. for two layer separation. However, the solvent did not separate into two layers and thus could not be purified.

Comparative Example 9

Purification was carried out in exactly the same manner as in Example 9, except that the γ-butyrolactone solvent was allowed to stand for 30 minutes for two layer separation. However, the solvent did not separate into two layers and thus could not be purified.

INDUSTRIAL APPLICABILITY

The present inventions according to claim 1 through 7 increase the yield of 2,2,2-trifluoroethanol, facilitates the separation of the salt byproducts and allows the recycling of the collected aprotic polar solvent.

The present inventions according to claim 8 through 12 allows the production of a γ-hydroxybutyric acid salt containing decreased amounts of EDCA. Such a γ-hydroxybutyric acid salt is better suited for the production of 2,2,2-trifluoroethanol.

When used in the hydrolysis of 1,1,1-trifluoroethyl chloride, a γ-hydroxybutyric acid salt produced according to the invention of claim 13 facilitates the separation of salt byproducts after 2,2,2-trifluoroethanol has been collected and allows the remaining solution to be recycled without any processings. As a result, the loss of the solvent during the process is reduced and the separation of the salt byproducts has become easy. In addition, the salt byproducts can be used in fertilizers.

The inventions according to claims 14 through 18 allow the removal of EDCA and/or EDCAM byproducts from the γ-butyrolactone to serve both as a reactant and a solvent and allow the collected γ-butyrolactone to be recycled as many times as desired. Specifically, the γ-butyrolactone collected after used in the hydrolysis of 1,1,1-trifluoroethylchloride is purified by the two-layer separation. As a result, the loss of the solvent during the process is reduced and the separation of the salt byproducts has become easy. In addition, the salt byproducts can be used in fertilizers.

The invention claimed is:

1. A method for producing 2,2,2-trifluoroethanol comprising reacting 1,1,1-trifluoro-2-chloroethane with a γ-hydroxybutyric acid salt-material system comprising an aprotic polar solvent and a γ-hydroxybutyric acid salt to generate 2,2,2-trifluoroethanol, wherein the γ-hydroxybutyric acid salt-material system comprises no more than 6 wt % of 4,4'-oxybis(butyric acid).

2. The method for producing 2,2,2-trifluoroethanol according to claim 1, wherein the reaction of the γ-hydroxybutyric acid salt-material system and 1,1,1-trifluoro-2-chloroethane results in a reaction mixture comprising 2,2,2-trifluoroethanol, and wherein a solution remaining in a still after 2,2,2-trifluoroethanol has been removed by distillation from the reaction mixture is reused as the aprotic polar solvent.

3. The method for producing 2,2,2-trifluoroethanol according to claim 1, wherein the γ-hydroxybutyric acid salt-material system is prepared by reacting, in the aprotic polar solvent, γ-butyrolactone with at least one member selected from the group consisting of an alkali metal hydroxide, an alkali metal carbonate, an alkaline earth metal hydroxide and an alkaline earth metal carbonate to create a reaction mixture, and dehydrating the reaction mixture, during or after the reaction, to a water concentration of 0.2 to 8 wt % at a temperature of 170° C. or below.

4. The method for producing 2,2,2-trifluoroethanol according to claim 1, wherein the aprotic polar solvent is γ-butyrolactone.

5. The method for producing 2,2,2-trifluoroethanol according to claim 3, wherein the alkali metal is potassium.

6. The method for producing 2,2,2-trifluoroethanol according to claim 3, wherein the dehydration is achieved by reduced-pressure distillation carried out at 150° C. or below.

7. The method for producing 2,2,2-trifluoroethanol according to claim 3, wherein the dehydration is completed within a time period of 15 hours or less.

8. A method for producing a γ-hydroxybutyric acid salt-material system, comprising reacting γ-butyrolactone, in an aprotic polar solvent, with at least one member selected from the group consisting of an alkali metal hydroxide, an alkali metal carbonate, an alkaline earth metal hydroxide and an alkaline earth metal carbonate to create a reaction mixture, and dehydrating the reaction mixture, during or after the reaction, to a water concentration of 0.2 to 8 wt % at a temperature of 170° C. or below.

9. The method for producing a γ-hydroxybutyric acid salt-material system according to claim 8, wherein the aprotic polar solvent is γ-butyrolactone.

10. The method for producing a γ-hydroxybutyric acid salt-material system according to claim 8, wherein the alkali metal is potassium.

11. The method for producing a γ-hydroxybutyric acid salt-material system according to claim 8, wherein the dehydration is achieved by reduced-pressure distillation carried out at 150° C. or below.

12. The method for producing a γ-hydroxybutyric acid salt-material system according to claim 8, wherein the dehydration is completed within a time period of 15 hours or less.

13. A method for producing 2,2,2-trifluoroethanol, comprising reacting the γ-hydroxybutyric acid salt-material system produced by the method according to claim 8 with 1,1,1-trifluoro-2-chloroethane.

14. A method for producing 2,2,2-trifluoroethanol comprising:
reacting a γ-hydroxybutyric acid salt-material system comprising γ-butyrolactone and potassium γ-hydroxybutyrate with 1,1,1-trifluoro-2-chloroethane to obtain a reaction mixture comprising 2,2,2-trifluororethanol;
separating 2,2,2-trifluoroethanol by distillation from the reaction mixture to obtain a solution comprising potassium chloride byproducts and 4,4'-oxybis(butyric acid) in a still,
removing potassium chloride byproducts from the still solution to obtain a solvent;
removing 4,4'-oxybis(butyric acid) by allowing the solvent to stand to separate it into two layers, one of which is a solution comprising γ-butyrolactone;
collecting the resulting γ-butyrolactone solution; and
recycling the collected γ-butyrolactone solution as a material for potassium γ-hydroxybutyrate and/or the γ-butyrolactone of the γ-hydroxybutyric acid salt-material system.

15. The method for producing 2,2,2-trifluoroethanol according to claim 14, wherein the collected γ-butyrolactone solution contains no more than 6 wt % of 4,4'-oxybis(butyric acid).

16. The method for producing 2,2,2-trifluoroethanol according to claim 14, wherein the removal of 4,4'-oxybis(butyric acid) by the two-layer separation is carried out at a temperature of 0° C. to 50° C.

17. The method for producing 2,2,2-trifluoroethanol according to claim 14, wherein the solvent is allowed to stand for at least one hour.

18. The method for producing 2,2,2-trifluoroethanol according to claim 14, wherein the γ-hydroxybutyric acid salt-material system comprises a reaction mixture obtained by mixing the collected γ-butyrolactone solution with an aqueous solution of potassium hydroxide and subsequently dehydrating the mixture.

19. The method for producing 2,2,2-trifluoroethanol according to claim 2, wherein the γ-hydroxybutyric acid salt-material system is prepared by reacting, in the aprotic polar solvent, γ-butyrolactone with at least one member selected from the group consisting of an alkali metal hydroxide, an alkali metal carbonate, an alkaline earth metal hydroxide and an alkaline earth metal carbonate to create a reaction mixture, and dehydrating the reaction mixture during or after the reaction, to a water concentration of 0.2 to 8 wt % at a temperature of 170° C. or below.

20. The method for producing 2,2,2-trifluoroethanol according to claim 2, wherein the aprotic polar solvent is γ-butyrolactone.

21. The method for producing 2,2,2-trifluoroethanol according to claim 3, wherein the aprotic polar solvent is γ-butyrolactone.

22. The method for producing 2,2,2-trifluoroethanol according to claim 4, wherein the dehydration is achieved by reduced-pressure distillation carried out at 150° C. or below.

23. The method for producing 2,2,2-trifluoroethanol according to claim 5, wherein the dehydration is achieved by reduced-pressure distillation carried out at 150° C. or below.

24. The method for producing 2,2,2-trifluoroethanol according to claim 4, wherein the dehydration is completed within a time period of 15 hours or less.

25. The method for producing 2,2,2-trifluoroethanol according to claim 5, wherein the dehydration is completed within a time period of 15 hours or less.

26. The method for producing 2,2,2-trifluoroethanol according to claim 6, wherein the dehydration is completed within a time period of 15 hours or less.

27. The method for producing a γ-hydroxybutyric acid salt-material system according to claim 9, wherein the dehydration is achieved by reduced-pressure distillation carried out at 150° C. or below.

28. The method for producing a γ-hydroxybutyric acid salt-material system according to claim 10, wherein the dehydration is achieved by reduced-pressure distillation carried out at 150° C. or below.

29. The method for producing a γ-hydroxybutyric acid salt-material system according to claim 9, wherein the dehydration is completed within a time period of 15 hours or less.

30. The method for producing a γ-hydroxybutyric acid salt-material system according to claim 10, wherein the dehydration is completed within a time period of 15 hours or less.

31. The method for producing a γ-hydroxybutyric acid salt-material system according to claim 11, wherein the dehydration is completed within a time period of 15 hours or less.

32. A method for producing 2,2,2-trifluoroethanol, comprising reacting the γ-hydroxybutyric acid salt-material system produced by the method according to claim 9 with 1,1,1-trifluoro-2-chloroethane.

33. A method for producing 2,2,2-trifluoroethanol, comprising reacting the γ-hydroxybutyric acid salt-material system produced by the method according to claim 10 with 1,1,1-trifluoro-2-chloroethane.

34. A method for producing 2,2,2-trifluoroethanol, comprising reacting the γ-hydroxybutyric acid salt-material system produced by the method according to claim 11 with 1,1,1-trifluoro-2-chloroethane.

35. A method for producing 2,2,2-trifluoroethanol, comprising reacting the γ-hydroxybutyric acid salt-material system produced by the method according to claim 12 with 1,1,1-trifluoro-2-chloroethane.

36. The method for producing 2,2,2-trifluoroethanol according to claim 15, wherein the removal of 4,4'-oxybis(butyric acid) by the two-layer separation is carried out at a temperature of 0° C. to 50° C.

37. The method for producing 2,2,2-trifluoroethanol according to claim 15, wherein the solvent is allowed to stand for at least one hour.

38. The method for producing 2,2,2-trifluoroethanol according to claim 16, wherein the solvent is allowed to stand for at least one hour.

39. The method for producing 2,2,2-trifluoroethanol according to claim 15, wherein the γ-hydroxybutyric acid salt-material system comprises a reaction mixture obtained by mixing the collected γ-butyrolactone solution with an aqueous solution of potassium hydroxide and subsequently dehydrating the mixture.

40. The method for producing 2,2,2-trifluoroethanol according to claim 16, wherein the γ-hydroxybutyric acid salt-material system comprises a reaction mixture obtained by mixing the collected γ-butyrolactone solution with an aqueous solution of potassium hydroxide and subsequently dehydrating the mixture.

41. The method for producing 2,2,2-trifluoroethanol according to claim 17, wherein the γ-hydroxybutyric acid salt-material system comprises a reaction mixture obtained by mixing the collected γ-butyrolactone solution with an aqueous solution of potassium hydroxide and subsequently dehydrating the mixture.

* * * * *